(12) United States Patent
Martin et al.

(10) Patent No.: US 8,025,397 B2
(45) Date of Patent: Sep. 27, 2011

(54) RETAINERS

(76) Inventors: Charlie Martin, Lexington, KY (US);
Mike McCullough, Edinburgh, IN (US);
Tony McCullough, Shelbyville, IN (US)

( * ) Notice: Subject to any disclaimer, the term of this patent is extended or adjusted under 35 U.S.C. 154(b) by 20 days.

(21) Appl. No.: 12/653,658

(22) Filed: Dec. 16, 2009

(65) Prior Publication Data

US 2010/0165286 A1    Jul. 1, 2010

Related U.S. Application Data

(60) Provisional application No. 61/201,912, filed on Dec. 16, 2008, provisional application No. 61/215,643, filed on May 7, 2009.

(51) Int. Cl.
*G02C 3/00* (2006.01)

(52) U.S. Cl. .................................... 351/157; 351/158
(58) Field of Classification Search .................... 351/41, 351/111, 156–158
See application file for complete search history.

(56) References Cited

U.S. PATENT DOCUMENTS

| 4,881,803 A * | 11/1989 | Giles et al. ............ 351/156 |
| 5,541,677 A * | 7/1996 | Huhtala ............... 351/156 |
| 2010/0283962 A1* | 11/2010 | Williams ............. 351/157 |

* cited by examiner

*Primary Examiner* — Huy K Mai
(74) *Attorney, Agent, or Firm* — Stockwell & Smedley, PSC

(57) ABSTRACT

Safety equipment includes both a securing apparatus for glasses or eyewear and having incorporated therein hearing protection devices. In particular, the hearing protection devices and the way in which they are connected may vary in numerous ways to provide flexible, simple, and convenient safety equipment.

19 Claims, 13 Drawing Sheets

RETAINERS

RELATED APPLICATIONS

The present application claims priority to patent applications Ser. Nos. 61/201,912 (filed Dec. 16, 2008) and 61/215,643 (filed May 7, 2009), both of which are incorporated by reference in their entirety.

BACKGROUND OF THE INVENTION

1. Field of the Invention

The present invention relates generally to wearable safety equipment and, more particularly, to an apparatus that may provide ear and eye protection.

2. Description of Related Art

Equipment that aids in protecting people under potentially dangerous conditions comes in a variety of forms and provide a variety of functions. However, safety equipment is only effective if it actually worn and properly used. And even though a person may know it is better for them to use safety equipment in a particular situation, everyone does not always do so. The excuses or rationalizations for doing so are numerous and sometimes are the fault of the person; however, the safety equipment itself can contribute to a person's reluctance to use it because it is cumbersome, easy to forget, or difficult to use.

Two particular areas of safety equipment that are typically useful are hearing protection and eye protection. Safety glasses or regular eyewear are useful in a wide variety environments to help protect a wearer's eyes from debris, dust, flying particles and the like. A retaining strap of some sort is particularly useful in that it helps keep the eyewear in place around a person's neck and it helps keep the eyewear securely in place when the eyewear is being used. Ear protection is another useful type of safety equipment that comes in a wide variety of styles. Individual foam ear plugs are useful but can be easily forgotten and, even if remembered, are typically stuffed in a person's pocket from where they need to be retrieved before being useful.

There have been previous attempts to address the issues described above such as U.S. Pat. Nos. 5,541,677 and 6,604,823. However, these attempts also have certain drawbacks. In particular, ease of adjustment and potentially unsafe configurations are drawbacks exhibited by the devices described in those patents. There remains, therefore, an unmet need for a combination eyewear retainer and ear protection device that provides improved safety, simplicity, flexibility, and ready customization for various sized users.

BRIEF SUMMARY OF THE INVENTION

Embodiments of the present invention relate to safety equipment that includes both a securing apparatus for glasses or eyewear and having incorporated therein hearing protection devices. In particular, the hearing protection devices and the way in which they are connected may vary in numerous ways to provide flexible, simple, and convenient safety equipment.

It is understood that other embodiments of the present invention will become readily apparent to those skilled in the art from the following detailed description, wherein it is shown and described only various embodiments of the invention by way of illustration. As will be realized, the invention is capable of other and different embodiments and its several details are capable of modification in various other respects, all without departing from the spirit and scope of the present invention. Accordingly, the drawings and detailed description are to be regarded as illustrative in nature and not as restrictive.

BRIEF DESCRIPTION OF DRAWINGS

Various aspects of a eyeglass retainer and ear protection device, in accordance with the principles of the present invention, are illustrated by way of example, and not by way of limitation, in the accompanying drawings, wherein.

DETAILED DESCRIPTION OF INVENTION

The detailed description set forth below in connection with the appended drawings is intended as a description of various embodiments of the invention and is not intended to represent the only embodiments in which the invention may be practiced. The detailed description includes specific details for the purpose of providing a thorough understanding of the invention. However, it will be apparent to those skilled in the art that the invention may be practiced without these specific details. In some instances, well known structures and components are shown in block diagram form in order to avoid obscuring the concepts of the invention.

Figure 1:
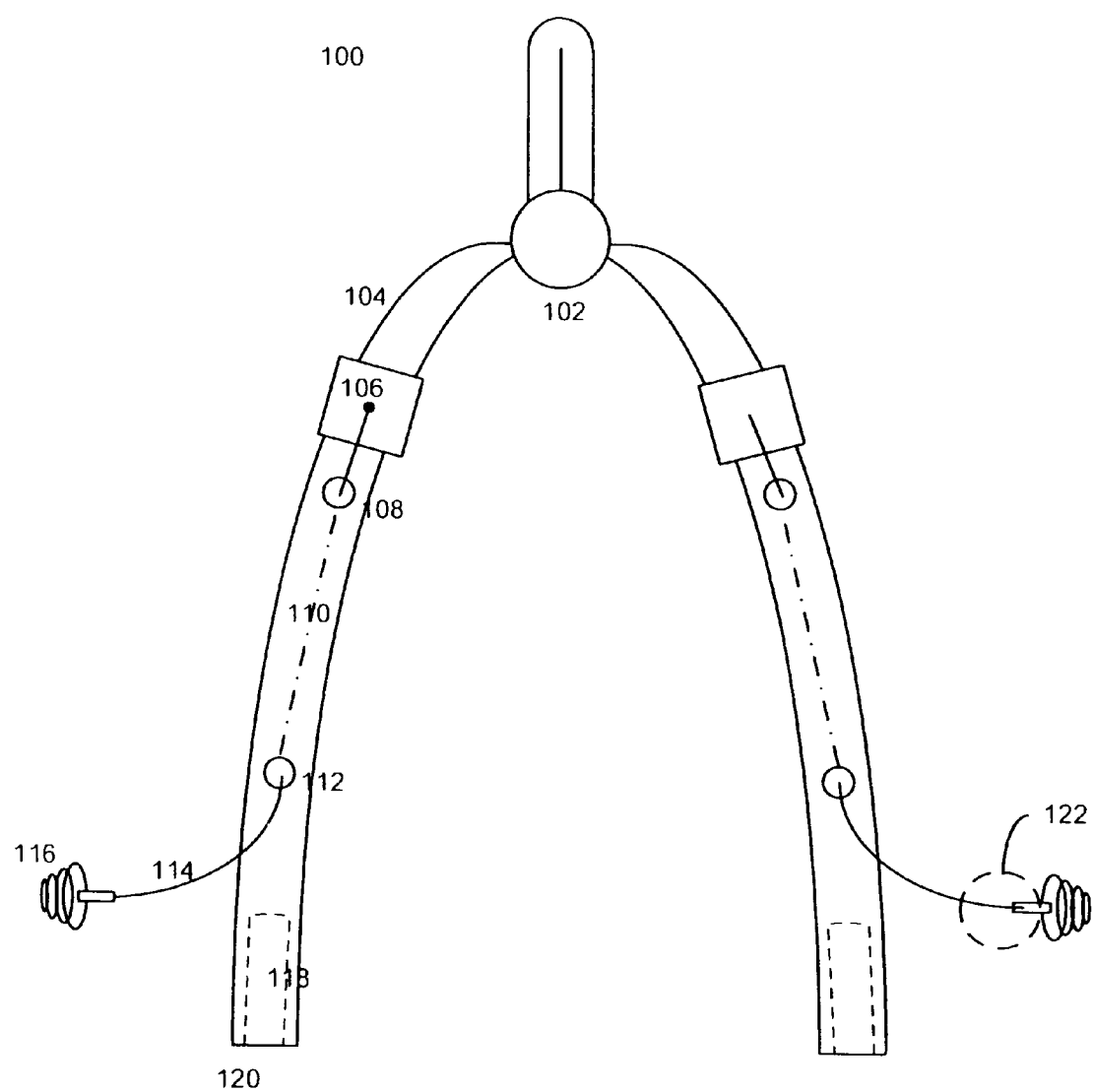
FIGS. 1-13 depict various embodiments of safety equipment in accordance with the principles of the present invention.

FIG. 1 illustrates an embodiment in accordance with the principles of the present invention. In general, the device 100 includes a left strap 104 and a substantially identical right strap. The relative lengths of the right and left straps can be controlled by placement of the ball 102. There are a variety of different adjustable balls 102 that are contemplated. For example, the ball 102 may include a spring-biased portion that presses inwardly on the straps so that the ball 102 is held in place. A user can depress such a portion, thereby biasing the portion away from the straps so that the ball 102 may be slid up and down on the straps. In that way, the length of the left and right straps may be adjusted. One of ordinary skill will recognize that other sizing mechanisms, such as clips, and sliders, may be substituted without departing from the scope of the present invention.

The left strap 104 includes an end portion 120 that is configured to accept the arm portion of various eyewear. Such eyewear can include sunglasses, goggles, safety eyewear and conventional eyewear. For example, the end portion 120 may include a cavity 118 that fits around the tip of the arm of a pair of glasses. This cavity 118 may be sized to provide a snug fit around the tip which is simply pushed into the cavity 118 by a user. The end of the portion 120 where cavity 118 is may also be constructed from an elastic material so as to accept a variety of sizes of glasses and still provide a snug fit.

Ear protection includes an ear plug 116 that can be permanently or replaceably attached to a cord 114. The cord 114 passes through a lower opening 112 and includes a portion 110 that is within the strap 104 and which exits out an upper opening 108. An end of the cord 114 is attached to a sliding mechanism 106.

In operation, the sliding mechanism may be slid upwardly or downwardly on the strap 104 so as to control the amount of play in the cord 114. In this way, the ear plug 116 may be positioned in a wearer's ear and the cord 114 adjusted so that it is positioned closely to the wearer's head so as to minimize the likelihood of it being entangled in, or caught by, other devices. Because the device 100 may sometimes be worn in an environment where the user is also wearing gloves, especially bulky gloves, the sliding mechanism 106 may be sized large enough to allow for potentially limited dexterity of the user.

The earplug on the right strap is substantially identical and is not discussed explicitly herein. However, by separating the ear plugs in this manner, they may be individually adjusted to accommodate a wide variety of circumstances. For example, it may be useful to wear an earplug in only one ear to facilitate conversation using the other ear. Thus, the lengths of the cord 114 for each side may be individually adjusted so that one ear plug may be used while the other one is completely withdrawn so that it provides no opportunity for snagging or entanglement with its surrounding.

The ear plug 116 may be any of a variety of available ear plugs. In particular, silicone, rubber, PVC, or foam. Some types of earplugs may be reusable, may be cleanable, or may be disposable. The connection area 122 between the cord and the earplug can be accomplished in a variety of ways without departing from the scope of the present invention. In particular, the cord may have an end much like a shoestring in which a tip is encapsulated or otherwise made harder. This tip can then be easily inserted and removed from a sleeve like member at the end of the ear plug. Thus, the cord's tip allows easy insertion and removal with the ear plug but the cord itself remains relatively flexible. Of course, other functionally equivalent ways of releasably connecting the ear plug 116 with the cord 114 are possible and are contemplated within the scope of the present invention.

The placement of the holes 108 and 112 and the amount of cord 114 that is available may all be varied without departing from the scope of the present invention.

As for materials of any of the straps 104, the earplugs 116 or the cord 114, one of ordinary skill will recognize that such materials may be selected to accommodate the anticipated environment in which the device 100 may be used. For example, in a painting environment where silicone may be very undesirable, the earplugs 116 would be selected from another more appropriate material. Also, in environments where electromagnetic waves may be present, the inclusion of metal and other conductive materials may be avoided. If an outdoor or harsh environment is contemplated, then the materials are selected to be rugged enough to withstand that environment. The need to be waterproof, heat resistant, chemical resistant, mold or bacteria resistant, and the like may all be considerations in determining the most appropriate material for the various components of the device 100. Furthermore, the device 100 may be constructed so as to be buoyant enough to float so that any attached glasses or eyewear may be easily retrieved if dropped in a liquid.

In the following figures, other variations and embodiments of the present invention are illustrated and discussed. In general, these variations relate to the manner in which the eyewear may attach to the device 100 or the way in which the ear protection is configured and secured. One of ordinary skill will recognize that only a limited number of the many permutations of the different components are illustrated and discussed. However, the present invention is not intended to be limited to only the explicitly illustrated embodiments. The variety of different components and elements illustrated in the 13 attached figures may also be arranged in ways not explicitly illustrated but nevertheless contemplated within the scope of the present invention. Also, in the discussions below and in the illustrations there is typically shown only one strap of the eyewear retaining device even though corresponding structures and functions are also present on the other strap as well.

Figure 2:
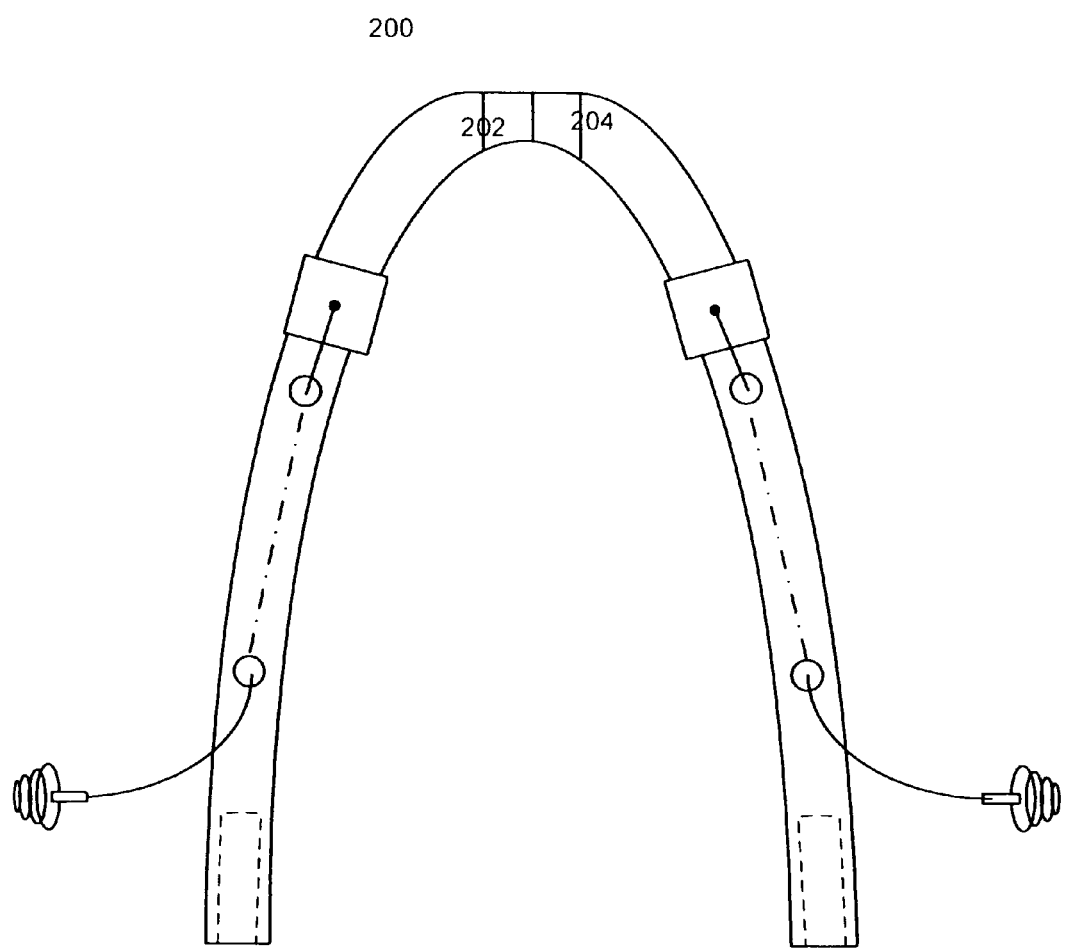

FIG. 2 illustrates an embodiment 200 in which the adjustable sizing mechanism of FIG. 1 has been replaced by a break-free structure. In the embodiment 200, a left half 202 and a right half 204 form a clasp that has a break-free characteristic. Because some of the environments in which the present device may be used are relatively dangerous, a break-free structure is useful to improve the overall safety of the device. As is known, the break-free structure may be designed for a variety of different break-free strengths so that if enough force is applied to one half relative to the other half, the portions 202 and 204 will separate thereby releasing the device 200 from around the body of a person wearing it. Such safety occurs whether the eyewear is actually being worn by the person or simply hanging around their neck. In embodiments with the break-free structure the benefits of having separate ear protection on each strap are particularly significant. The eyeglass retainer straps can be pulled apart for safety without interference from the presence of a earplug cord. The break-free structure is shown in the back of the device; however, the break-free structure could alternatively be positioned at other locations. For example, two break-free structures could be present with one on each strap relatively close to the eyeglasses.

Figure 3:
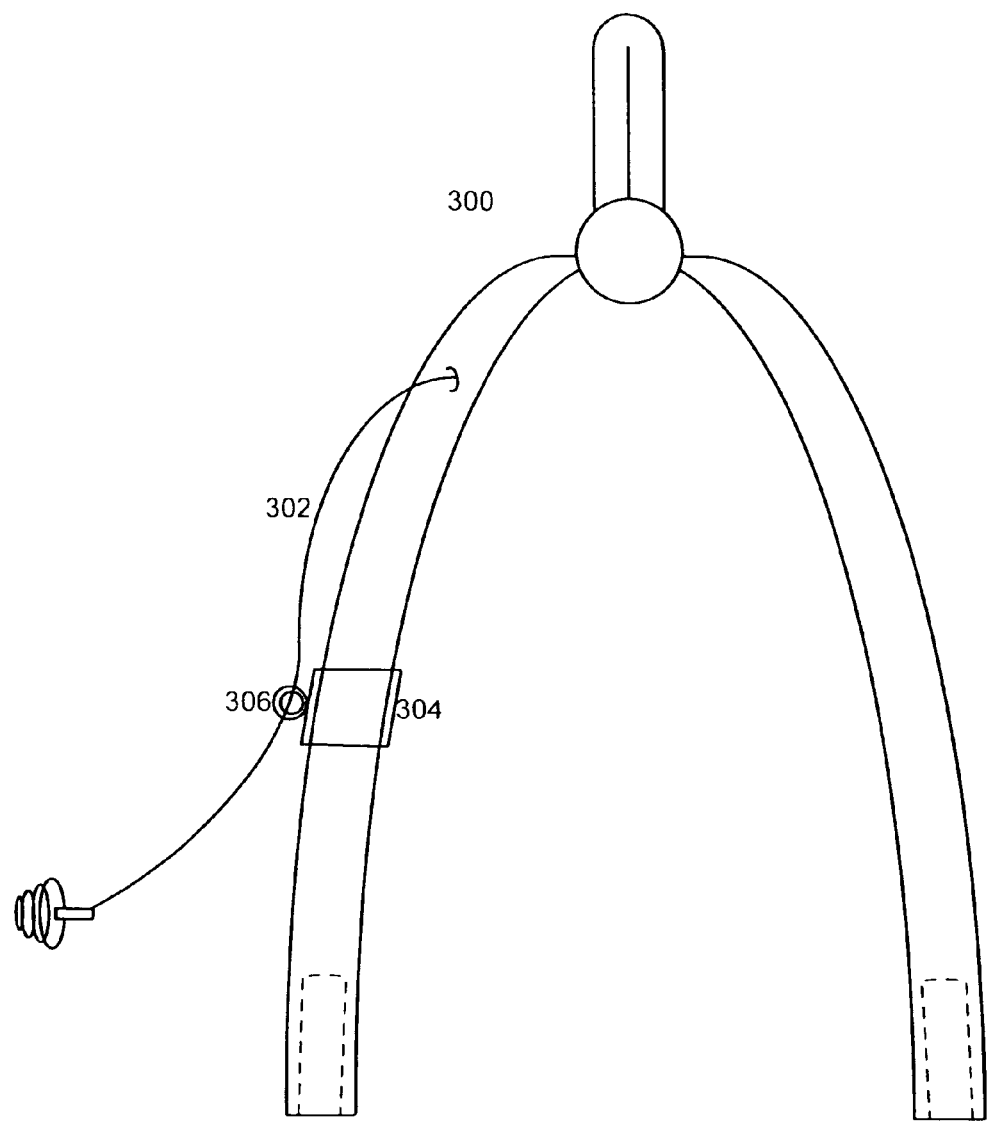

FIG. 3 illustrates an embodiment in which the cord 302 is fixed to the strap (the location of which may vary). A sliding device 304 is provided that fits around the strap and can be moved upwards or downwards. The sliding device 304 may, for example, be a clip, or a sleeve, that fits securely around the strap but that can be moved by a user applying enough force to cause sliding to take place. The sliding device 304 includes a clip 306 of some type that allows the cord 302 to enter and be securely held. In operation, the ear plug may be inserted in a wearer's ear and the sliding device 304 moved to a position that removes significant slack from the cord 302. When in storage, the sliding device 304 may be moved into position to keep the earplug and cord 302 close to the strap so that it is more easily untangled when desired for use.

Figure 4:
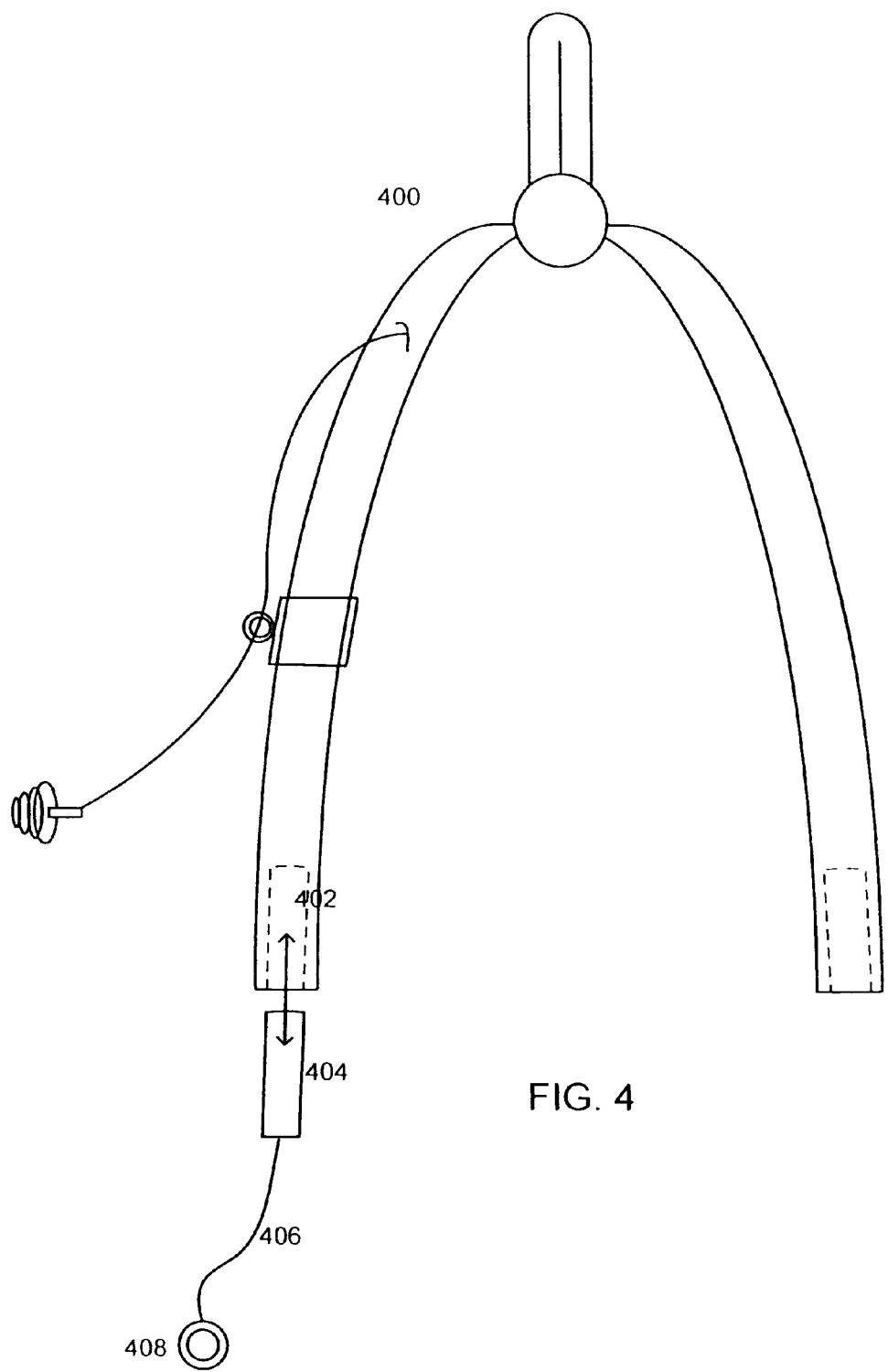

In FIG. 4, an embodiment 400 is shown in which the connector tip of the strap is configured to receive (and release) an insert rather than eyewear directly. For example, the cavity 402 is configured to cooperate with an insert 404. Thus, any type of connector for eyewear may be used as long as it is connected to the other end of the insert 404. For example, the embodiment 400 may be used with regular eyewear but may also be used with specialty eyewear by having an appropriate connector on end of the insert 404 opposite from the end of the insert 404 that fits within the cavity 402. In the specific embodiment of FIG. 4, the insert 404 is connected to a cord, chain, string, etc. 406 that has a lug 408 or similar device on its end. The lug 408 is what connects with the eyewear itself.

Figure 5:
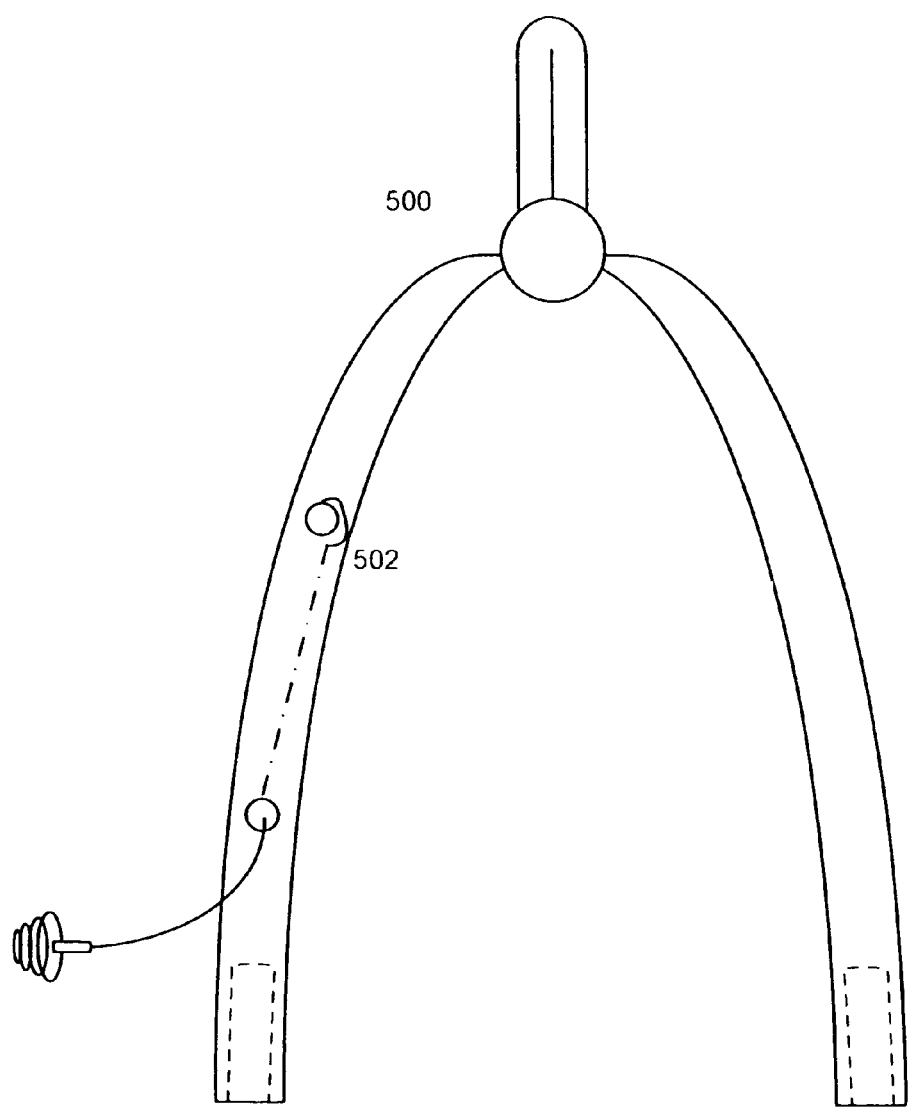

FIG. 5 illustrates an embodiment 500 in which a retractable spool mechanism 502 is included within the strap. Thus, the cord of the ear plug may be extended so that the ear plug will reach a person's ear but can be retraced around the spool 502 when not in use. Furthermore, the retractable spool mechanism 502 may have positive stops, or locks, so that ear plug remains at a fixed location until the user purposely retracts it. As mentioned earlier, although structures are shown in some of the figures as being part of only one of the straps, the present invention also contemplates similar, corresponding structures in the other strap as well.

Figure 6:
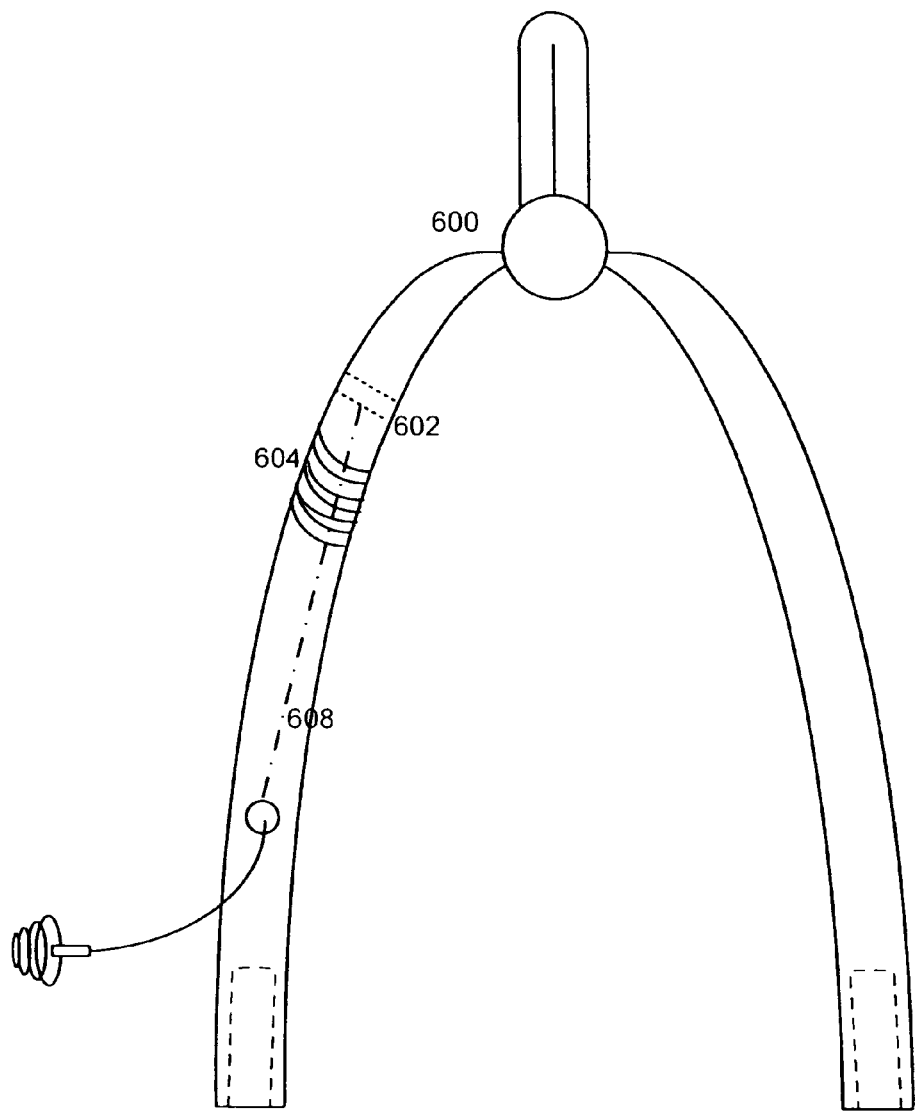
Figure 7:
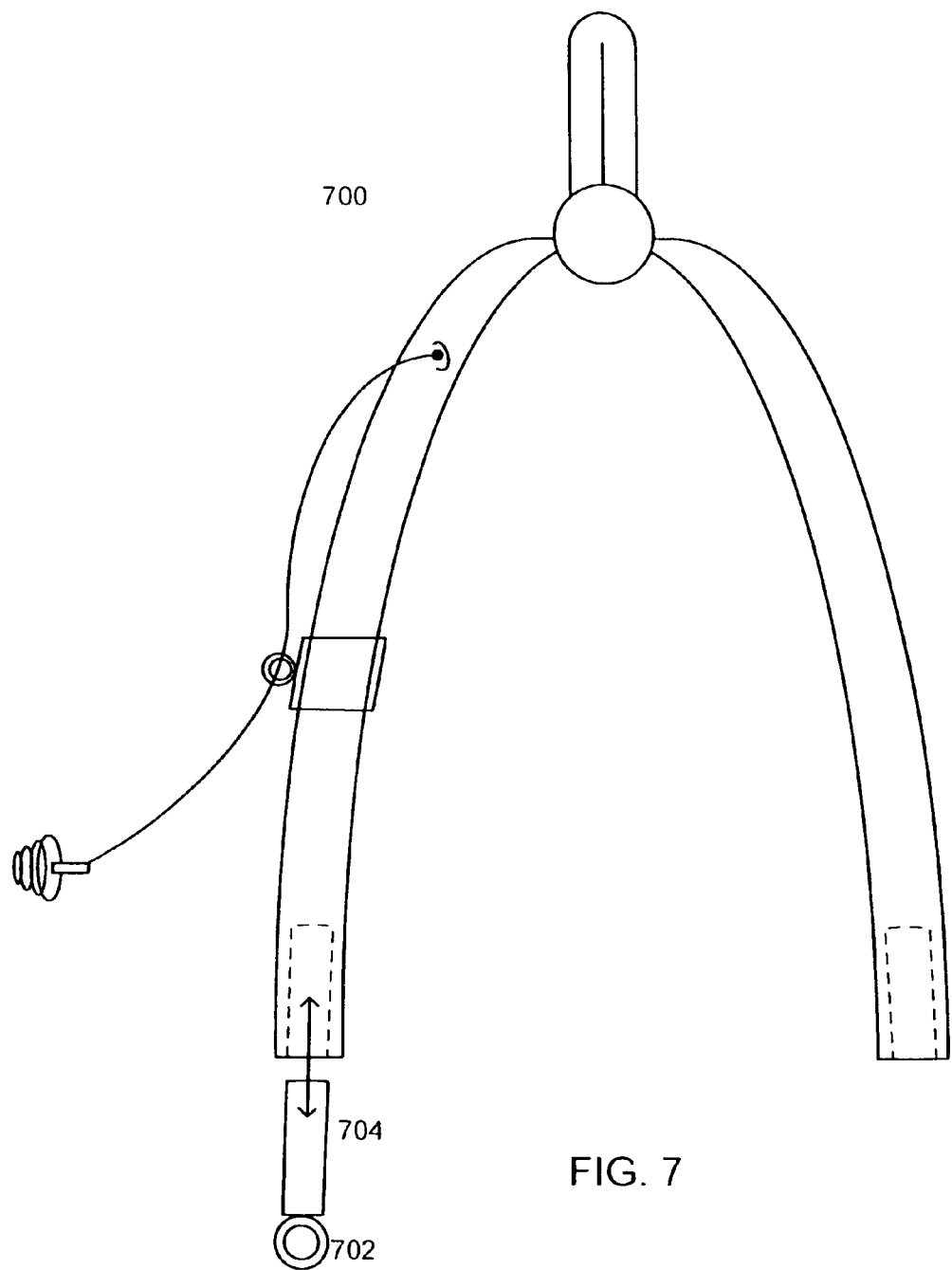

FIG. 6 illustrates an embodiment 600 in which the cord 608 may be retracted or extended as a result of the strap having an accordion-like section 604. A stop 602 holds the cord 608 in place relative to the accordion-like section 604. However, as the section 604 is stretched or compressed, the amount of cord 608 external to the strap changes accordingly. FIG. 7 depicts and embodiment 700 that is a variation of the eyewear connector of FIG. 4. In particular, one difference is that the lug connector 702 is coupled directly with the insert portion 704 and does not require the intervening chain, cord, string, etc. Again, this configuration allows a customized adapter (using an insert 704, and lug 702) to be utilized so that the straps may accommodate even specialized eyewear without any modification.

Figure 8:
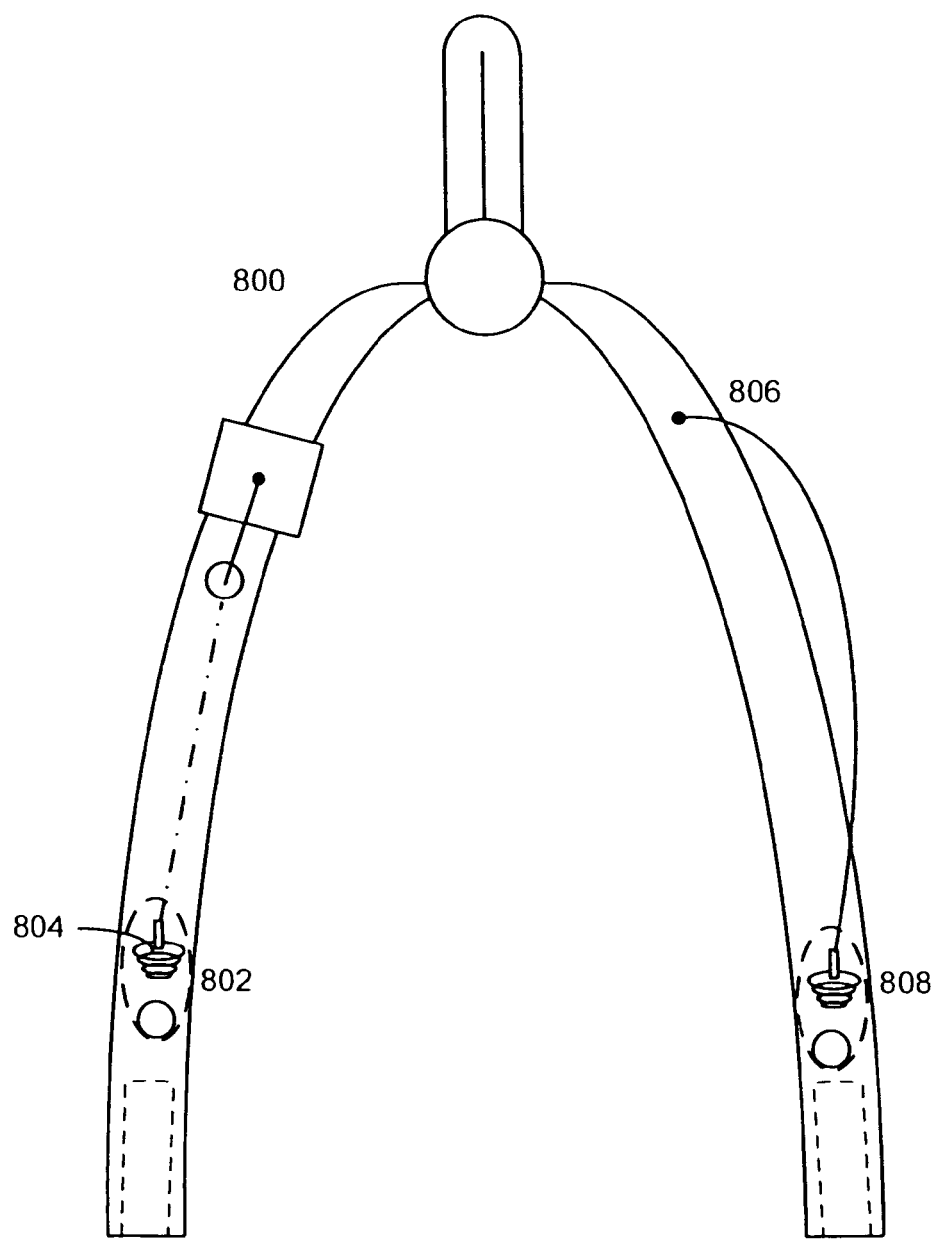

In FIG. 8, two different embodiments are shown on a single device 800 illustrating a new concept from the other embodiments. The new concept is that the ear plugs may reside internally within the device 800. In the left strap there is a pocket 802 formed within the strap in which the ear plug 804 fits. In the right strap, there is a similar pocket 808. When the ear plugs are needed, the user pushes the ear plugs from their respective pockets so that they exit out a hole in the strap and are ready for use. The different straps of FIG. 8 illustrate that pocket concept for the ear plugs is applicable to both an external cord 806 configuration as well as the internal, adjustable cord configuration of the left strap.

Figure 9:
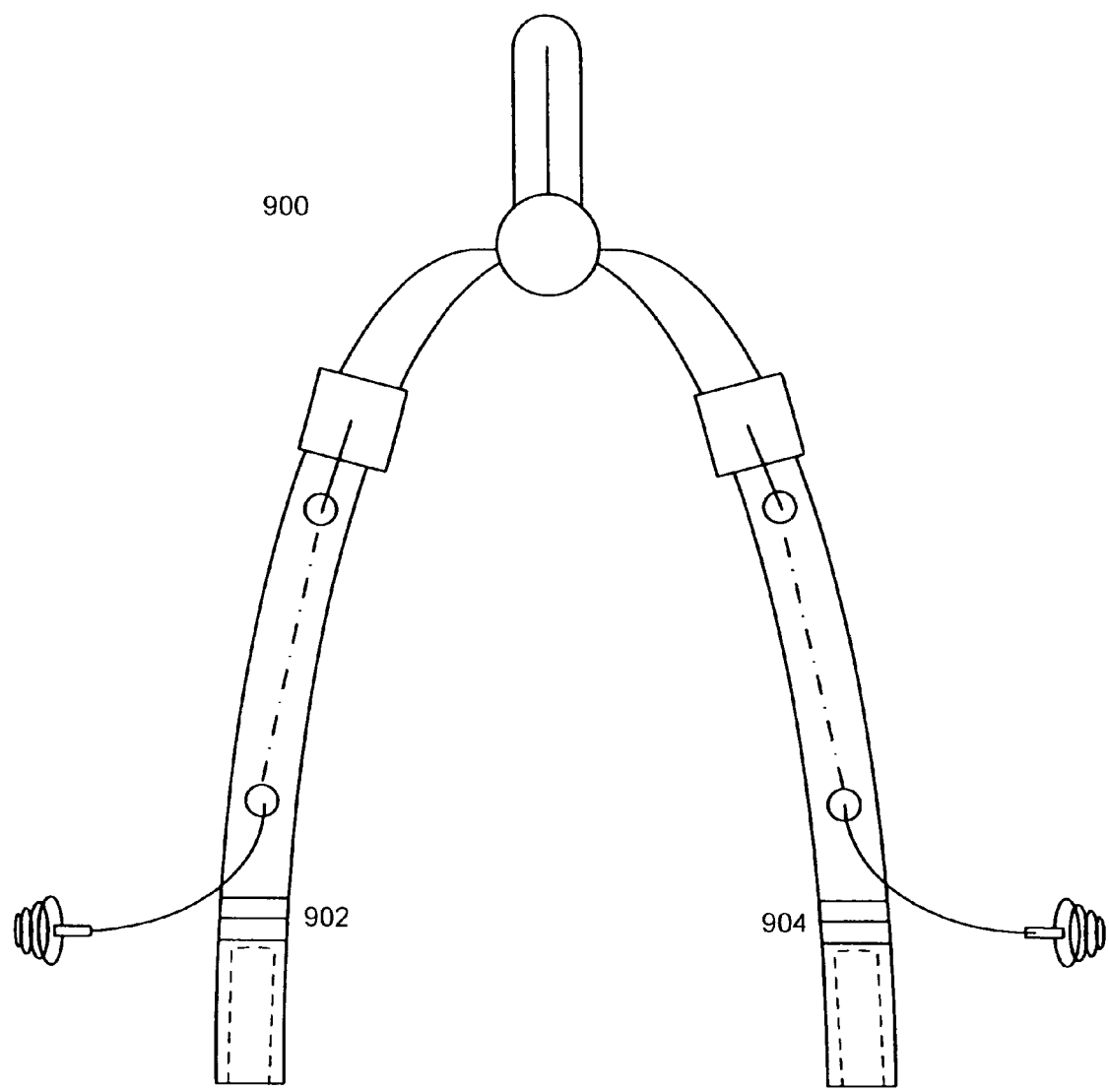

FIG. 9 depicts an embodiment 900 that includes both the break-free safety advantage as well as the adjustable strap advantage of FIG. 1. In particular, each strap includes a respective break-free connector 902 and 904. Thus, the device 900 performs similarly to the device described with respect to FIG. 1 but also provides additional safety features. If any portion of the strap or eyewear is snagged to a degree where the appropriate forces are applied to one of the break-free connectors 902, 904, then the device 900 is easily dislodged from the wearer without inflicting harm. As mentioned with respect to FIG. 2, various break-free connectors having a variety of attributes and characteristics are contemplated within the scope of the present invention.

Figure 10:
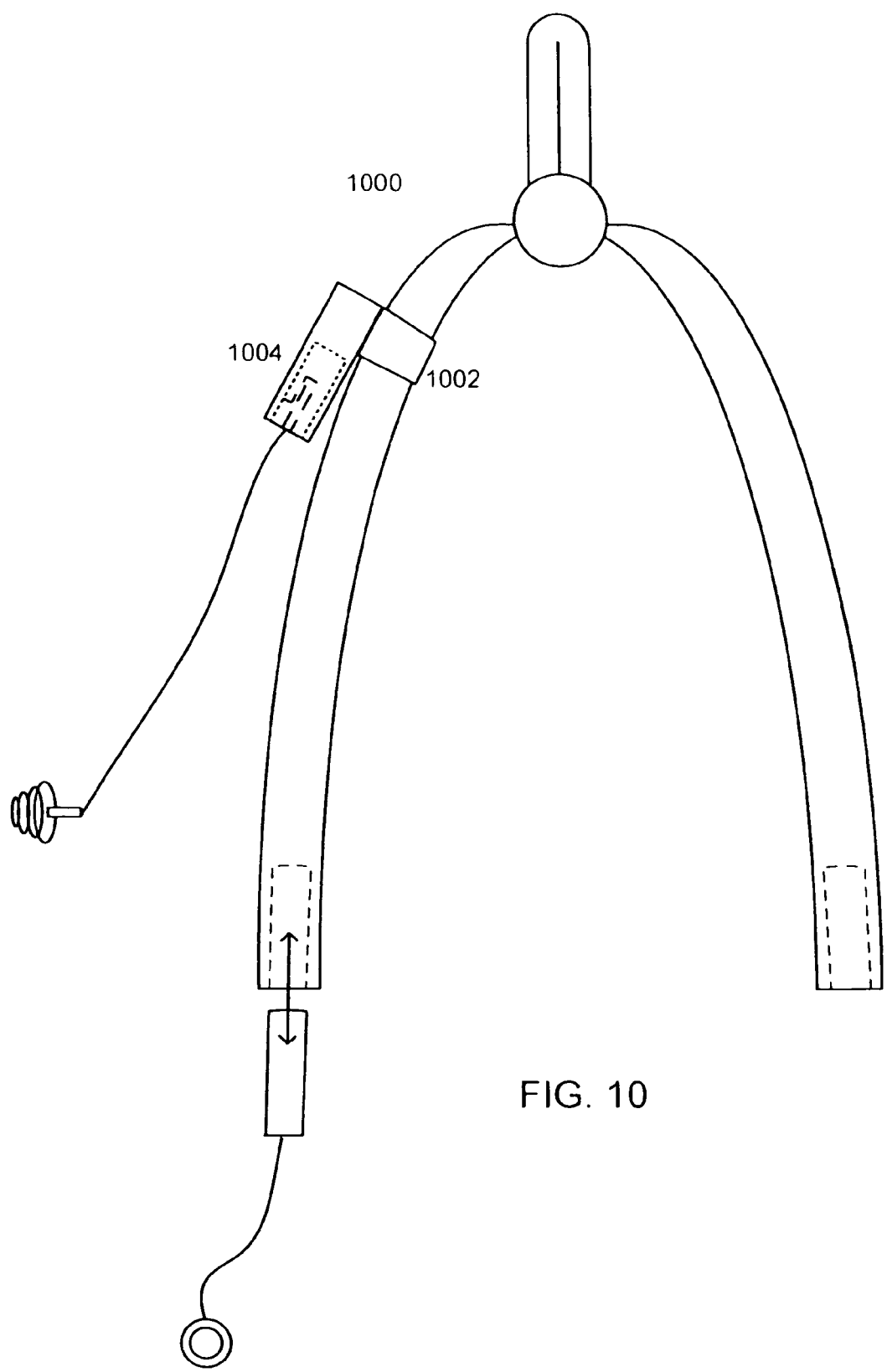

FIG. 10 illustrates an embodiment, in which the ear plug connector may be designed to allow easy customization. In the previous embodiments, the cords and ear plugs were relatively standard and although the ear plugs could be replaced, the cord was a relatively fixed item. In FIG. 10, an attachment 1002 may be fixedly or moveably attached to a strap of the device 1000. The attachment 1002 includes a clip portion 1004 that has a cavity which receives the ear plug component. As shown, the ear plug is attached to a cord and the end of the cord is inserted and securely held within the cavity of the clip portion 1004. However, other ear plug components may be used as well. One advantage is that a wider variety of cords and ear plugs may be used (and custom ones designed) as long as they have a standard insert that fits within the clip portion 1004. Another advantage is that the ear plug component may be removed and the device 1000 may act simply to retain the eyewear. All that remains is a relatively unobtrusive clip 1002 and attachment portion 1004 that does not interfere with other clothing, other machinery, or other safety equipment, When it is desirable to support hearing protection, then an ear plug component may me readily, simply, and easily added by inserting it within portion 1004.

Figure 11:
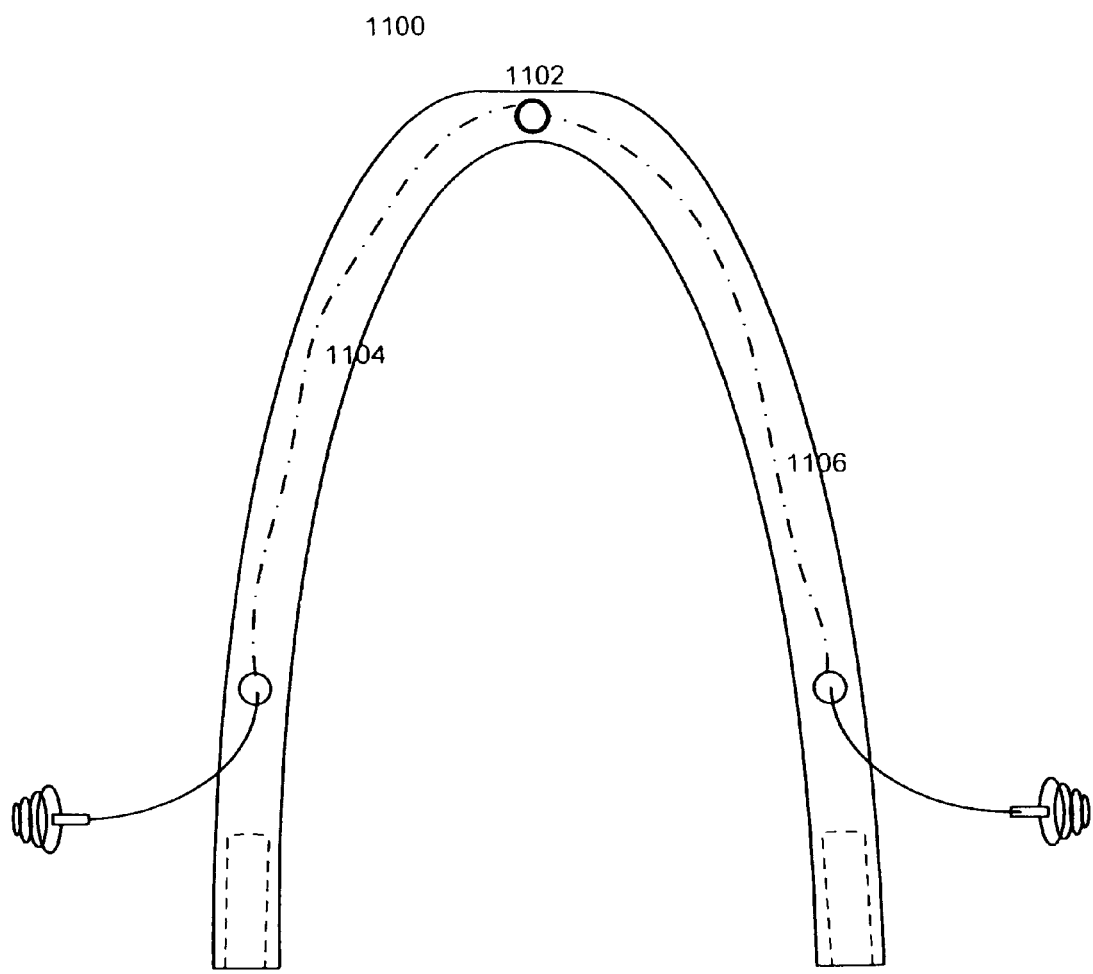
Figure 12:
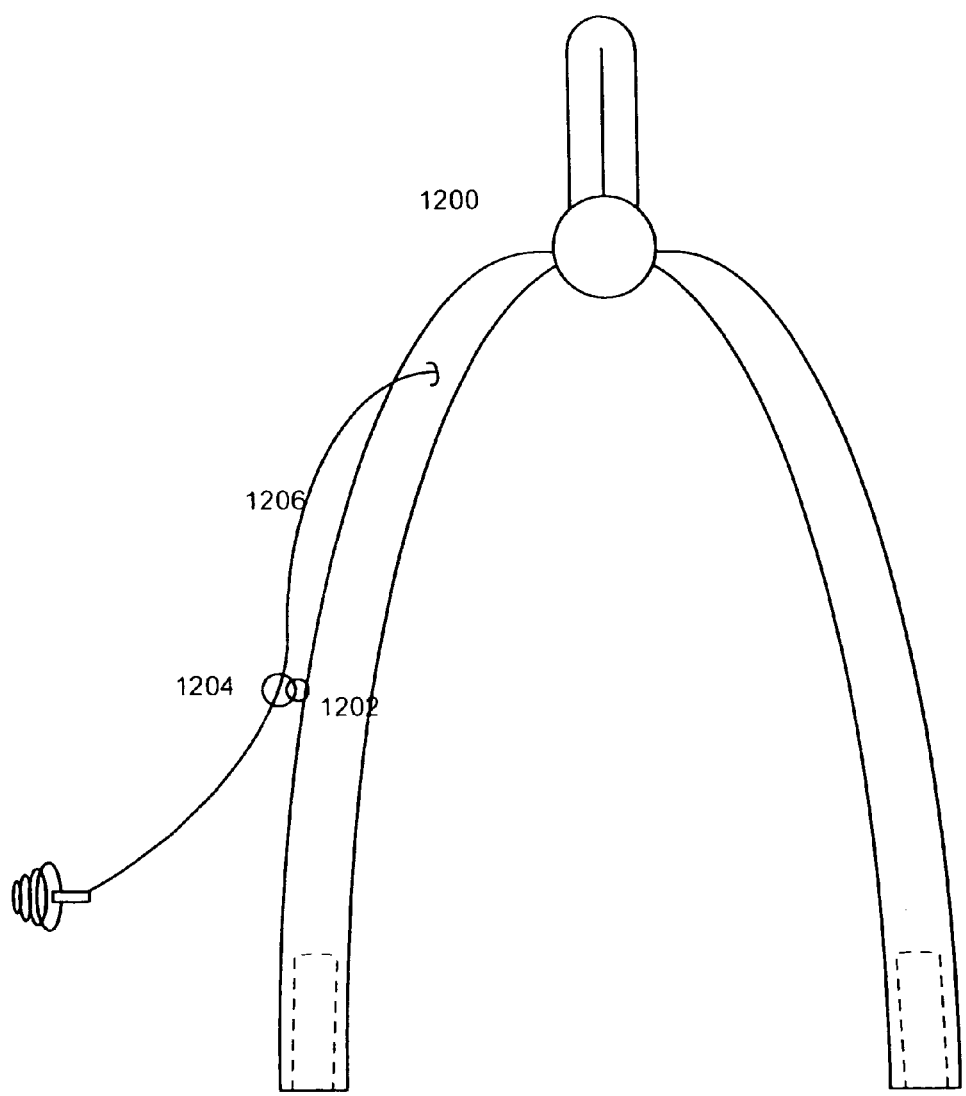

FIG. 11 includes a retractable spool 1102 located substantially at the center of the two straps of device 1100. The spool 1102 retracts the cord 1104 in one direction while also being able to retract the cord 1106 in an opposite direction. As is known in the art, the spool 1102 may operate so that cords 1104 and 1106 may be extended and retracted independently of one another. FIG. 12 depicts an embodiment 1200 in which the cord 1206 can be secured to the strap in at least two locations. The cord 1206 is attached near its top but it also includes a snap 1204, or similar device, that attaches to a cooperating structure 1202 that is fixed to the strap at a lower location. In this way, the cord 1206 is regularly located along most of its length in a secure manner close to the strap but can be easily released to allow use of the ear plug. The location of the snap 1204 and cooperating structure 1202 may be located at various locations along the length of the strap and the cord 1206. Also, the snap 1204 may be adjustable up and down the length of the cord 1206 so as to provide customization by each user. One of ordinary skill will appreciate that a wide variety of structures may be substituted for the snap 1204 (such as, for example, Velcro) without departing from the scope of the present invention.

Figure 13:
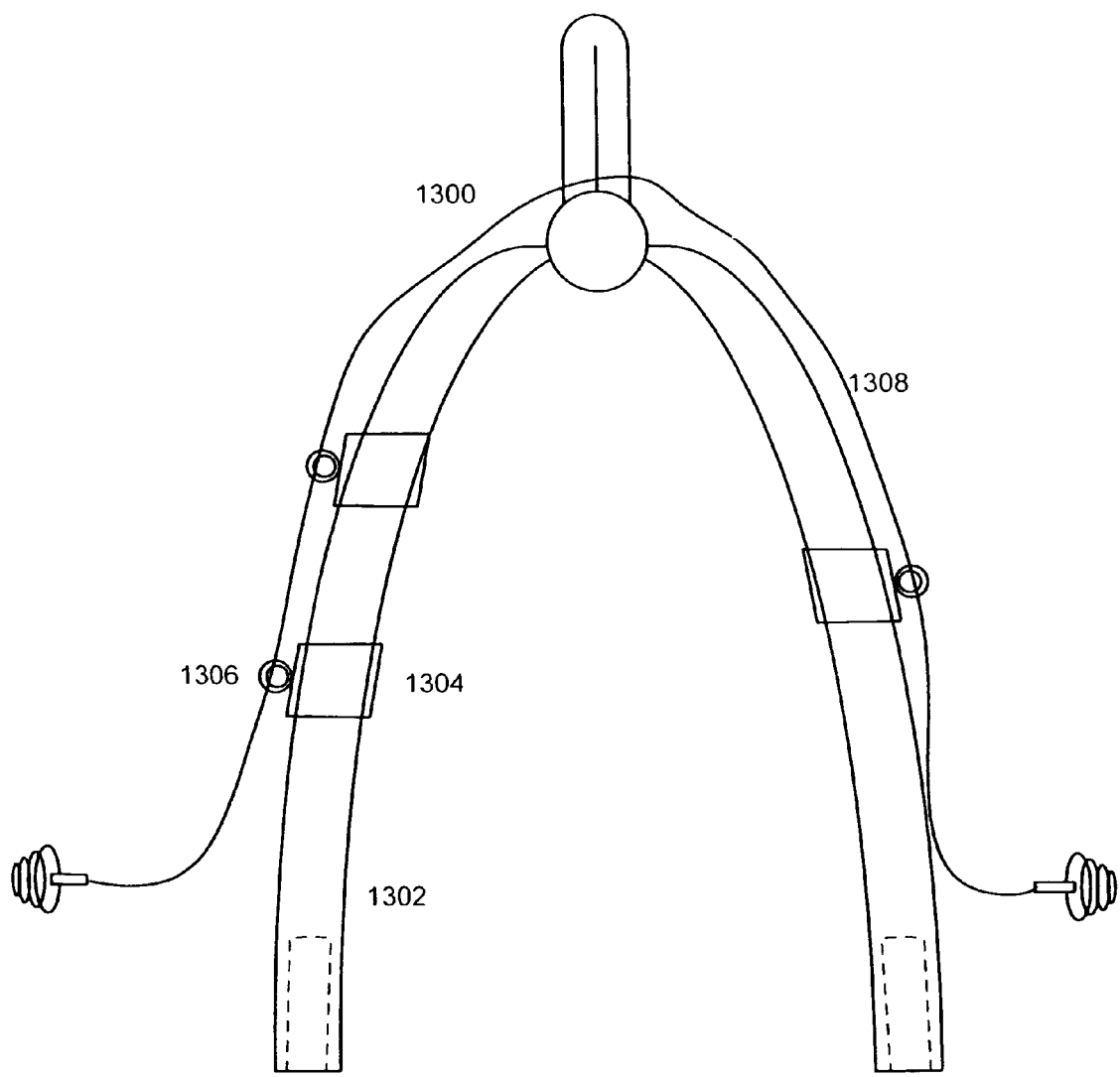

FIG. 13 depicts an embodiment 1300 that is a variation of the general concepts illustrated in FIG. 3. In FIG. 13, the ear plugs are not necessarily an integral part of the eyewear retainer device. For example, there are a variety of ear plugs (usually, but not always, disposable) that include a cord that connects two ear plugs (this assembly is 1308 of FIG. 13). The embodiment of FIG. 13 allows use of such ear plugs with an eyewear retainer. In particular, a clip assembly includes a first portion 1304 that attaches to the strap of the eyewear retainer and a second portion 1306 that accepts the cord of the earplug assembly 1308. It is advantageous that the second portion 1306 be configured to securely hold the cord but also allow for its simple release. Similarly, the first portion 1304 may be configured to securely attach to the retainer strap but also be releasable. Thus, the embodiment 1300 may be configured to be a) be an eyewear retainer, b) an eyewear retainer with one or more clips, or c) an eyewear retainer with one or more clips that hold ear plugs. The number of clips used may vary from one to many. One exemplary number of clips is five—this would allow two clips along each side and one near the rear.

In the previous description, the end of respective ear plug cords which is opposite the ear plug connects to each strap in either a permanent manner or a releasable manner. For example, an end of the ear plug cord can attach to a strap using a snap mechanism, a rivet-like mechanism or a clip mechanism. In may be beneficial that this attachment mechanism allows rotation of the cord relative to the strap so that movement of the cord has little effect on the strap connected to the eyeglasses. The ear plug cord could also be connected to the strap using a hook and loop system. For example, the end opposite the ear plug could have a hook (or loop) portion and the strap have a complementary loop (or hook) portion. Furthermore, the strap could have the loop (or hook) portion extends a length along the strap or have multiple loop (or hook) portions. In this way, the ear plug cord having the hook (or loop) portion could connect to the strap and different locations. Also, if the ear plug cord had multiple hook (or loop) portions then it could stay connected to the strap at multiple points.

In addition to ear plugs that connect to the straps, the straps could include various rings, clips or pockets that allow other things to be attached to the straps. For example, a ring (any shaped open structure) could be on each side of the eyeglass retaining strap which would allow a cord with a clip to be easily attached to each side of the strap. The cords attached in this way could have an ear plug on the end opposite the end that attaches to the strap but other types of devices could be attached to end of the cords as well. Thus, the presence of one or more rings on each side of the retaining strap would allow earplug or other items to be easily clipped or attached to the strap. The rings, as mentioned above, are not necessarily round but could be triangular, square, rectangular, etc. As for a specific location, the ring could be located anywhere along the length of each half of the strap. Thus, there would be strap material extending from the end with the eyeglasses to the ring and then the same, or different, strap material from the ring to the end of that half of the strap. Thus, the center of the ring is relatively free of strap material so that a clip can be easily attached.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with each claim's language, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. An eyeglass retainer comprising:
a strap including a left half and a right half;
the left half including a first end and second end, wherein first end of the left half is configured to connect to a first eyeglass arm;
the right half having a first end and a second end, wherein the first end of the right half is configured to connect to a second eyeglass arm;
a right cord having a first end and second end, wherein the first end of the right cord is coupled with the right half and the second end of the right cord is coupled to a first ear plug; and
a left cord, unconnected to the right cord, having a first and second end, wherein the first end of the left cord is coupled with the left half and the second end of the left cord is coupled to a second ear plug.

2. The eyeglass retainer of claim 1, comprising:
a right slider coupled with the right half and configured to slide along the right half between the first and second ends of the right half and wherein the first end of the right cord is connected to the right slider; and
a left slider, independent of the right slider, coupled with the left half and configured to slide along the left half between the first and second ends of the left half and wherein the first end of the left cord is connected to the left slider.

3. The eyeglass retainer of claim 1, wherein:
the right half includes a first opening proximate the first end of the right half and a second opening between the first opening of the right half and the second end of the right half and wherein a portion of the right cord extends inside the right half between the first and second openings of the right half; and
the left half includes a first opening proximate the first end of the left half and a second opening between the first opening of the left half and the second end of the left half and wherein a portion of the left cord extends inside the left half between the first and second openings of the left half.

4. The eyeglass retainer of claim 1, further comprising:
a break-free structure coupling the second end of the right half with the second end of the left half.

5. The eyeglass retainer of claim 1, wherein:
the first end of the left cord is coupled to the left half with a left releasable connector; and
the first end of the right cord is coupled to the right half with a right releasable connector.

6. The eyeglass retainer of claim 5, wherein:
the second end of the right cord is releasably coupled to the first ear plug thereby allowing the first ear plug to be removable; and
the second end of the left cord is releasably coupled to the second ear plug thereby allowing the second ear plug to be removable.

7. The eyeglass retainer of claim 1, wherein:
a right retraction mechanism within the right half configured to retract a portion of the right cord inside the right half; and
a left retraction mechanism within the left half configured to retract a portion of the left cord inside the left half.

8. The eyeglass retainer of claim 1, wherein:
a first location where the first end of the right cord is coupled with the right half, the first location being adjustable along a length of the right half between the first end of the right half and the second end of the right half; and
a second location where the first end of the left cord is coupled with the left half, the second location being adjustable along a length of the left half between the first end of the left half and the second end of the left half.

9. The eyeglass retainer of claim 1, further comprising:
a length adjuster through which the right half and left half pass, the length adjuster configured to slide along the left half and right half such that a first distance between the first end of the right half and the length adjuster is varied and a second distance between the first end of the left half and the length adjuster is varied.

10. The eyeglass retainer of claim 1, wherein:
the first end of the right cord includes one of a loop and a hook connector and the right half includes at least one portion having an opposite one of the loop and hoop connector.

11. The eyeglass retainer of claim 1, further comprising:
a first right clip coupled with the right half, the first right clip shaped and configured to secure a first portion of the right cord proximate to a first portion of the right half; and
a first left clip coupled with the left half, the first left clip shaped and configured to secure a first portion of the left cord proximate a first portion of the left half.

12. The eyeglass retainer of claim 10, further comprising:
a second right clip coupled with the right half, the second right clip shaped and configured to secure a second portion of the right cord proximate to a second portion of the right half; and
a second left clip coupled with the left half, the second left clip shaped and configured to secure a second portion of the left cord proximate to a second portion of the left half.

13. The eyeglass retainer of claim 1, wherein:
the first end of the left half includes a left opening configured to receive the first eyeglass arm; and
the first end of the right half includes a right opening configured to receive the second eyeglass arm.

14. The eyeglass retainer of claim 1, wherein:
the first end of the left half is elastic and configured to fit over the first eyeglass arm; and the first end of the right half is elastic and configured to fit over the second eyeglass arm.

15. The eyeglass retainer of claim 1, wherein:
the right half includes a right pocket configured to hold the first ear plug; and
the left half includes a left pocket configured to hold the second ear plug.

16. An eyeglass retainer comprising:
a strap including a left half and a right half;
the left half including a first end and second end, wherein first end of the left half is configured to connect to a first eyeglass arm;
the right half having a first end and a second end, wherein the first end of the right half is configured to connect to a second eyeglass arm;
a first right clip coupled with the right half, the first right clip shaped and configured to secure a first portion of a cord proximate to a first portion of the right half; and
a first left clip coupled with the left half, the first left clip shaped and configured to secure a second portion of the cord proximate a first portion of the left half.

17. The eyeglass retainer of claim 16, further comprising:
a second right clip coupled with the right half, the second right clip shaped and configured to secure a third portion of the cord proximate to a second portion of the right half; and
a second left clip coupled with the left half, the second left clip shaped and configured to secure a fourth portion of the cord proximate to a second portion of the left half.

18. The eyeglass retainer of claim 17, further comprising:
a rear clip coupled with the right half, the rear clip shaped and configured to secure a fifth portion of the cord proximate to a third portion of the right half opposite the first end of the right half.

19. The eyeglass retainer of claim 17, further comprising:
a rear clip coupled with the left half, the rear clip shaped and configured to secure a fifth portion of the cord proximate to a third portion of the left half opposite the first end of the left half.

* * * * *